United States Patent
Coupard et al.

(10) Patent No.: US 9,234,158 B2
(45) Date of Patent: Jan. 12, 2016

(54) PROCESS FOR PRETREATMENT OF VEGETABLE OILS BY HETEROGENEOUS CATALYSIS OF THE ESTERIFICATION OF FATTY ACIDS

(71) Applicant: IFP Energies Nouvelles, Rueil-Malmaison Cedex (FR)

(72) Inventors: Vincent Coupard, Villeurbanne (FR); Laurent Bournay, Chaussan (FR); Eszter Toth, Lyons (FR); Sylvie Maury, Saint Maurice d'Argoire (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 14/570,094

(22) Filed: Dec. 15, 2014

(65) Prior Publication Data
US 2015/0175932 A1  Jun. 25, 2015

(30) Foreign Application Priority Data
Dec. 19, 2013 (FR) ...................................... 13 63080

(51) Int. Cl.
| | |
|---|---|
| *C11C 3/00* | (2006.01) |
| *C07C 67/08* | (2006.01) |
| *C11B 1/02* | (2006.01) |
| *C11C 3/10* | (2006.01) |
| *B01J 8/02* | (2006.01) |

(52) U.S. Cl.
CPC .................. *C11C 3/003* (2013.01); *C07C 67/08* (2013.01); *C11B 1/02* (2013.01); *C11C 3/10* (2013.01); *B01J 8/025* (2013.01); *B01J 2208/00628* (2013.01)

(58) Field of Classification Search
None
See application file for complete search history.

(56) References Cited

U.S. PATENT DOCUMENTS

| | | | |
|---|---|---|---|
| 7,456,305 B2 * | 11/2008 | Piacentini et al. | ....... B01J 23/06 554/167 |
| 8,536,357 B2 | 9/2013 | Dietrich et al. | |
| 2009/0294358 A1 | 12/2009 | Dietrich et al. | |
| 2012/0255223 A1 | 10/2012 | Kaul et al. | |

FOREIGN PATENT DOCUMENTS

GB          2169895 A        7/1986

OTHER PUBLICATIONS

Search Report and Opinion from corresponding French Patent Application No. 13/63080 dated Sep. 30, 2014.

* cited by examiner

*Primary Examiner* — Yate K Cutliff
(74) *Attorney, Agent, or Firm* — Millen White Zelano and Branigan, PC; John Sopp; Anthony Zelano

(57) ABSTRACT

The invention relates to a continuous process for pretreatment of an oil feedstock comprising at most 20% by weight of free fatty acids by esterification of free fatty acids in which a vertical liquid/liquid contactor containing an esterification catalyst in solid form is supplied in counter-current by an alcohol feedstock comprising at least 20% by weight of an alcohol and said oil feedstock, with said contactor being operated at a temperature of between 25 and 120° C., with said contactor performing the contact in liquid-liquid counter-current between a heavy phase and a light phase, with said heavy phase being able to be either an oil-rich phase or an alcohol-rich phase.

10 Claims, No Drawings

PROCESS FOR PRETREATMENT OF VEGETABLE OILS BY HETEROGENEOUS CATALYSIS OF THE ESTERIFICATION OF FATTY ACIDS

FIELD OF THE INVENTION

This invention relates to a vegetable oil pretreatment process, in which the fatty acids that are present are esterified by heterogeneous catalysis in a liquid-liquid contactor operating in counter-current.

PRIOR ART

Within an international context marked by the rapid growth in demand for fuel, in particular for diesel-based fuels and kerosene in the European Community, the search for new renewable energy sources constitutes a major issue.

Among the feedstocks obtained from renewable resources, the use of animal or vegetable oils, optionally semi-refined, is often recommended.

Poorly adapted to the direct supply of modern diesel engines of particular vehicles, these oils, consisting essentially of triglycerides, should be transformed by, for example, transesterification or else by undergoing a hydrotreatment stage, for obtaining high-quality fuel bases that comply in particular with specifications, directly or after mixing with other fractions obtained from the refining of crude oil.

The increase in costs of raw materials of biological origin and the recent debate on first-generation biofuels necessitates both the diversification of triglyceride sources (*Jatropha curcas*, for example) but also the use of less refined raw materials for improving the overall yield of the branch or else the use of low-value by-products obtained from the farm produce industry such as slaughterhouse fats from poultry, sheep, and cattle, as well as the cooking oils used.

The raw oil is obtained by pressing the oleaginous seed and washing it with water. The oleaginous seed is heated and then pressed to obtain the pressurized oil. The remaining solid material that still has a very high level of fatty substance undergoes a solvent extraction stage, most often of hexane; the oil that is obtained after evaporation of hexane is called extraction oil.

The extraction oil is then mixed with water. Water and oil are compounds that are not very soluble. This addition of water will be accompanied by the appearance of an aqueous phase in which the water-soluble compounds that are present (phospholipids, mucilages) will dissolve. This two-phase mixture is then separated by centrifuging, and the fatty phase is called raw oil. The stages described above can differ according to the treated oleaginous seeds; however, by raw oil, one skilled in the art means an oil that has undergone no other treatment than washing with water and then centrifuging to remove a major portion of the water-soluble compounds.

These oils consist for the most part of triglycerides at a level of 80-98% by weight. The minor compounds, i.e., present at a level of 2 to 20% by weight, are (for example and in a nonlimiting way) free fatty acids, mono- and di-glycerides, oxide compounds of glycerides obtained from the degradation of the oil, polymers, waxes (natural hydrocarbons that are present in the oil), proteins that contain sulfur and/or nitrogen, phospholipids, tocopherols, sterols, natural dyes as well as more or less volatile odorous compounds. Among the other minor compounds, radicals that comprise heteroelements such as phosphorus, magnesium, calcium, iron or zinc are also included, with the content of said radicals able to go up to 2,500 ppm. In the case of phosphorus, magnesium, and calcium, these radicals are primarily in the form of phospholipids and/or sterols. In the particular case of magnesium, these radicals are present in the pigments. In the case of iron and/or zinc, these radicals can be in the form of sterols and/or soaps (Oils and Fats Manual: A Comprehensive Treatise, Volume 1, page 90, Karleskind, A. et al.).

Semi-refined oil means a raw oil as defined above that has undergone a pre-refining stage for the purpose of eliminating the minority compounds, and in particular at least a portion of phospholipids and at least a portion of free fatty acids. The pre-refining of a raw oil generally comprises:

A demucilagination stage consisting of the elimination of at least a portion of the phospholipids or mucilages by precipitation in the presence of acidulated water;

A stage for neutralization, in the presence of a soda solution, of demucilaginated oil making it possible to neutralize at least a portion of the free fatty acids that are present in the oil. The neutralization pastes formed during this stage are generally separated by centrifuging and entrain a portion of impurities contained in the oil, and A stage for washing with water to eliminate the traces of sodium salts, And a vacuum drying stage.

The semi-refined oil that has undergone these stages is also called a DNS (demucilaginated, neutralized and dried) oil. Said semi-refined oil can also contain up to 20 ppm of phosphorus, calcium, magnesium, iron and/or zinc, in the form of phospholipids (Oils and Fats Manual: A Comprehensive Treatise, Volume 1, page 90, Karleskind, A. et al.), as well as free fatty acids.

However, the fatty acids have a negative impact on the existing technologies for the transformation of oils—used oils obtained from the industries of farm produce and catering and oils of animal origins (suet, fats from poultry, sheep and cattle)—into fuel. In particular, the fatty acids that are present can have a corrosive effect on the preheating sequences (case of the hydrotreatment of vegetable oils) and can cause a loss in yield (case of the homogeneous transesterification processes) or a shortening of the service life of the catalyst and a loss of performances (case of the heterogeneous transesterification processes). They can be extracted upstream from the units for transformation of vegetable oils into fuel by all conventional treatments, for example by neutralization as explained above. The primary drawback of this technique comes from the fact that the extracted fatty acids are then non-upgraded fuel by-products, which brings about a significant loss in material yield and therefore significantly hampers the economy of industries for production of biofuels from vegetable oils. This effect will be all the more significant as the content of fatty acids in the starting oil increases. Another solution consists in esterifying the fatty acids into fatty acid esters according to the reaction:

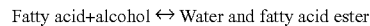

The esterification, by transforming the fatty acid of upgradable ester into fuel fractions, makes it possible to improve the yield of transformation of oil into fuel by 1 to 20% relative to the treatments whose purpose is to extract the fatty acid that then becomes a non-upgraded by-product for the fuel fraction.

Esterification is a reaction that is known and documented in the literature or recent patents. It is a matter of a balanced reaction. It is therefore necessary to remove a reaction product for advancing the conversion. The evaporation of water, for example, is a customary means of achieving this balance shift. With methanol being more volatile than water, it should be evaporated in advance, during an operation that is generally done under vacuum (generally on the order of 100 millibars for preventing increasing to temperatures able to bring about product losses by thermal degradation), which increases the energy costs of this type of process.

The conventional implementation is therefore in two reaction stages separated by a complete evaporation of water and unreacted methanol.

Commercial solutions have been developed for carrying out the esterification of free fatty acids on ion exchange resins. However, industrial implementation is not currently done because it is uneconomical.

In its brochure "BayFAME® Continuous Free Fatty Acid Esterification," Bayer Technology Service describes a process that makes it possible to treat all of the acidic oil feedstocks, having free fatty acid contents that can range up to 100%, i.e., containing only fatty acids, by esterification of said free fatty acids. The reaction is catalyzed by an acidic resin. The process is presented as a series of reaction stages, each reaction stage being followed by a stage of separation from the water+methanol fraction and a methanol/water separation, with the number of stages ranging from 1 to 3 based on the initial content of the fatty acid feedstock.

The patent applications WO09056230 A1 and WO09056231 A1 essentially teach the same principle: fatty acid is esterified by heterogeneous catalysis on an acidic resin. The reaction stage is followed by a stage for separation of water+methanol from the oil fraction, as well as a water/methanol separation.

Cairncross, R., Melick, C., "Novel Reactor Design for the Production of Biodiesel from Free Fatty Acids," AICHE 2008 meeting teaches the use of a bubble column in which the methanol vapor bubbles in a liquid phase containing fatty acids and oil and is to diffuse into this liquid so as to carry out the esterification reaction. A large excess of methanol is necessary, on the one hand, so that the methanol bubbles can pass through the column and so that a sufficient quantity of methanol is transferred in the oil phase, and, on the other hand, to take away the water that is formed during the reaction. In addition, in the case of a gas/liquid implementation (gas stream of methanol), it is necessary to have temperature and pressure conditions that make it possible to be placed above the bubble point of the methanol. The methanol is to pass into the liquid phase so that the reaction takes place, with the oleic acid being very sparingly volatile under the reaction conditions. The reaction volume is therefore limited to the volume of the liquid phase. This invention eliminates these drawbacks by proposing a liquid/liquid reaction between the methanol and the polluted oil of fatty acid. By diffusion, the two phases contain oleic acid and alcohol and are therefore the site of the esterification reaction. This is reflected in a gain in the compactness of the equipment used.

US 2010/0249442 describes the esterification of fatty acids in the presence of a polymeric and macroporous acidic resin, comprising free sulfonic groups. The esterification is carried out in a fixed bed in the presence of alcohol, with the fatty acids having been separated in advance from the oil that is to be treated, and then supplied in a mixture with alcohol in the fixed bed in co-current.

EP 0192135 describes the use of a strongly acidic ion exchange resin that contains free sulfonic acid groups on a polymer matrix for the esterification of fatty acids in a process where the oil and the alcohol are supplied in co-current in a fixed bed, with the water being separated at the end of the reaction.

An object of this invention is to propose a process for pretreatment of a raw or semi-refined oil, making it possible to transform the free fatty acids contained in said oil by esterification in such a way that the content of fatty acids in the oil pretreated by the process according to the invention is less at least at 1% by weight of the pretreated oil.

SUMMARY AND ADVANTAGE OF THE INVENTION

The process according to the invention makes it possible not to undergo the stress of the release of water on the reaction balance in the esterification reaction of the fatty acids. It therefore makes it possible to achieve very high conversion levels of fatty acids in a single reactive contactor and to avoid intermediate drying of the oil for removing this water that unfavorably influences the equilibrium of the reaction. This process also makes it possible to react the most refractory oil, i.e., the oil that is the poorest in free fatty acids, with the alcohol that is the poorest in water.

DETAILED DESCRIPTION OF THE INVENTION

This invention relates to a continuous process for pretreatment of an oil feedstock comprising at most 20% by weight of free fatty acids by esterification of free fatty acids in which a vertical liquid/liquid contactor containing an esterification catalyst in solid form is supplied in counter-current by an alcohol feedstock comprising at least 20% by weight of an alcohol and said oil feedstock, with said contactor being operated at a temperature of between 25 and 120° C., with said contactor performing the contact in liquid-liquid counter-current between a heavy phase and a light phase, with said heavy phase being able to be either an oil-rich phase or an alcohol-rich phase.

By pretreatment, it is understood that the process according to the invention is placed upstream from a process for treatment of vegetable oils and/or animal oils. In a preferred embodiment, said pretreatment process according to the invention is placed upstream from a process for hydrotreatment of the oils. In another preferred embodiment, said pretreatment process according to the invention is placed upstream from a process for transesterification of said oils in such a way as to produce alkyl esters.

The pretreatment process according to this invention therefore makes possible the use either of a raw animal or vegetable oil that has not undergone any pretreatment, or a semi-refined animal or vegetable oil for producing distillate bases (kerosene and diesel fuel).

Said oil feedstock consists of all sources containing triglycerides and free fatty acids. Preferably, said oil feedstock is a raw or semi-refined oil obtained from renewable plant sources of ground or aquatic origin, or an animal oil, as well as mixtures of such oils.

The plant oils of ground or aquatic origin are advantageously selected from among the following oils: palm, soybean, palm-kernel, coconut, babassu, canola, sunflower, corn, cottonseed; and the following oils: peanut, pourghere (*Jatropha curcas*), castor, linseed, and crambe; and all the oils obtained from, for example, sunflower or canola by genetic modification or hybridization or else originating from algae or aquatic organisms or from among the partially modified oils, for example by polymerization or oligomerization, such as, for example, the "stand oils" of linseed oil, sunflower oil, blown vegetable oils, used cooking oils, the by-products of the refining of oils: PFAD (Palm Fatty Acid Distillate) or broken pasta.

The animal oils are advantageously selected from among the animal fats and preferably from among lard and fats consisting of waste from the food industry or obtained from the catering industries, fatty suet, and slaughterhouse waste from poultry, swine, sheep and cattle. The densities at 15° C. of these oils are advantageously between 850 and 940 kg/m3, and their kinematic viscosities at 40° C. are between 20 and 400 mm2/s, and preferably between 30 and 50 mm2/s.

Said oil feedstock generally also comprises different impurities and in particular heteroatoms such as nitrogen and/or sulfur. The contents of nitrogen and sulfur in the feedstocks obtained from renewable sources are generally between approximately 1 ppm and 100 ppm by weight and preferably less than 100 ppm, according to their nature. They can reach up to 1% by weight in particular oils. The content of free fatty acids in said oil feedstock is at most 20% by weight.

Said alcohol feedstock comprises an alcohol that is selected from among ethanol and methanol. Said alcohol feedstock comprises at least 20% by weight of alcohol, preferably at least 30% by weight of alcohol, and in a preferred manner at least 40% by weight. Said alcohol feedstock also comprises 0 to 50% by weight of water, as well as impurities such as aldehydes, ketones, acids, whose content represents at most 1% by weight of said alcohol feedstock, and heteroelements such as Na, K, Al, Fe in ionic form at a content that is less than 500 ppm, preferably less than 100 ppm, with these heteroelements having a negative effect on the service life of the ion exchange resins that are advantageously used in the process according to the invention.

The ternary diagram (either methanol or ethanol)/water/ester shows that there exist conditions of temperature, pressure and composition for which these three elements form a single liquid phase, and others for which they form two phases: an alcohol-rich phase and an oil-rich phase. Rich is defined as that whose composition exceeds 50% by weight of the phase. Mention is made of separation conditions when the conditions of temperature, pressure and composition are such that two liquid phases coexist.

Thus, by selecting a set of advantageous operating conditions and a choice of a suitable alcohol level, conditions are established where the separation takes place and is maintained at any point of said liquid-liquid contactor. The coexistence of the two liquid phases makes it possible to implement a liquid/liquid counter-current.

The density of said alcohol feedstock varies based on respective alcohol and water contents in said feedstock. Thus, for low water contents, said alcohol feedstock will have a lower density than said oil feedstock. For high contents of water, said alcohol feedstock will have a higher density than said oil feedstock. In a preferred arrangement, the water content of said alcohol feedstock is adjusted in such a way that said alcohol feedstock has a density that is higher than that of said oil feedstock. In another preferred arrangement, the water content of said alcohol feedstock is adjusted in such a way that said alcohol feedstock has a density that is lower than that of said oil feedstock.

Below, light phase will be called the liquid phase whose density is the lowest, and heavy phase will be called the liquid phase whose density is the highest. Based on the water content of said alcohol feedstock, it can therefore constitute the light phase or the heavy phase.

Liquid/liquid counter-current is defined as a system in which two liquid phases circulate in counter-current relative to one another.

The contactor of the process according to the invention is placed vertically. It comprises at least two supply points and at least two draw-off points. Supply point is defined as a point by which a liquid phase enters into the contactor. Draw-off point is defined as a point by which a liquid phase is extracted from the contactor.

A heavy phase is supplied in said contactor at least one injecting point located above the supply point of a light phase. A light phase is drawn off from said contactor at at least one draw-off point located above at least one supply point of a heavy phase. A heavy phase is drawn off from said contactor at least one draw-off point located below at least one supply point of a light phase.

The oil-rich drawn-off phase, which will be, according to the water content of the alcohol feedstock, the light phase or the heavy phase, constitutes the pretreated oil effluent.

By differences in density, said light phase circulates in said contactor from the bottom to the top, while said heavy phase circulates in said contactor from the top to the bottom. The light phase and the heavy phase are therefore brought into contact in counter-current relative to one another.

Said contactor comprises a catalyst for esterification in solid form.

Said catalyst is kept in place in said contactor by any means that are known to one skilled in the art. It can be, for example, and in a non-limiting manner, placed in perforated baskets, in small stacked bags, or encapsulated in a structured packing.

Said catalyst is an acidic solid, preferably selected from among silica-aluminas, acidic clays, zirconia that may or may not be sulfated, and acidic resins, taken by themselves or in a mixture, and preferably from among the acidic resins.

Preferably, said catalyst has an acidic capacity, representing the number of active sites of said catalyst, metered by potentiometry during neutralization by a KOH solution (equivalent to the ASTM D2187 method), of 0.2 to 6 mmol of $H^+$ equivalent per gram, preferably 0.2 to 4.5, in a preferred manner 0.2 to 4.2, and in a very preferred manner 1.2 to 4.2 mmol of $H^+$ equivalent per gram.

Acidic solids that are commonly commercially available are clays that are treated with acids to make them acidic (such as montmorillonite).

An acidic resin that can advantageously be used as catalyst in the process according to the invention comprises sulfonic groups that are grafted on an organic substrate consisting of aromatic and/or haloaliphatic chains. It advantageously comprises between 1 and 2 terminal sulfonic groups per aromatic group and/or haloaliphatic group. Said acidic resin is prepared by polymerization or co-polymerization of aromatic vinyl groups following by sulfonation, with said aromatic vinyl groups being selected from among styrene, vinyl toluene, vinyl naphthalene, vinyl ethyl benzene, methylstyrene, vinyl chlorobenzene and vinyl xylene, with said resin having a cross-linking level of between 20 and 40%, preferably between 25 and 35%, and in a preferred manner between 30 and 35%. The size of the resin is between 0.15 and 1.5 mm. Size of the resin is defined as the diameter of the smallest sphere encompassing the resin particle. The resin size classes are measured by sieving procedures on suitable sieves according to a technique that is known to one skilled in the art.

A preferred resin is a resin that consists of aromatic monovinyl copolymers and aromatic polyvinyl copolymers, and, in a very preferred manner, divinylbenzene and polystyrene copolymers. For example, the resin is a TA801 resin sold by the Axens Company.

Said catalyst can occupy the entire section of said contactor. It is thus in contact both with the light phase and the heavy phase.

In a preferred arrangement, the heavy phase is rich in oil, and the light phase is rich in alcohol; i.e., the density of the alcohol feedstock is less than the density of the oil feedstock.

The esterification reaction takes place, within said contactor, primarily in the oil-rich phase. This reaction produces water that, by affinity with alcohol, diffuses into the alcohol-rich phase. The diffusion of this water increases the density of the alcohol-rich phase (light phase). The density of the alcohol feedstock that constitutes, in this preferred arrangement, the light phase is therefore to be low enough so that the density of the light phase at no time becomes higher than the density of the oil-rich phase, constituting the heavy phase. Actually, this inversion of the ratio of densities would cause a reversal of the direction of circulation of the phases and therefore the stopping of the operation of the liquid/liquid contactor.

In this preferred arrangement, said contactor advantageously comprises at least one zone for collecting the light phase, a zone for collecting the heavy phase, a zone for bringing said heavy phase into contact with said catalyst, and a zone for redispersion of the light phase and the heavy phase. Said collecting zone can be designed based on the principle of plates of gas/liquid distilling columns with a height for liquid maintenance.

Upon contact with the catalyst, the reaction for esterification between the free fatty acids and the alcohol contained in the light and heavy phases takes place. This reaction produces esters and water. Just as the alcohol passes from the alcohol-rich phase to the oil-rich phase by transfer of material, the water that is produced passes from the oil-rich phase to the alcohol-rich phase. Said water will therefore be separated from the oil and esters formed by the reaction.

Said oil-rich phase therefore gradually becomes depleted of free fatty acids and is enriched in esters. Since circulation is done in counter-current, said oil-rich phase is in contact with an alcohol-rich phase that becomes increasingly rich, i.e., containing less and less water.

Thus, this implementation in liquid-liquid counter-current makes it possible to bring into contact the oil that is the poorest in free fatty acids, i.e., the most difficult to treat, with the purest alcohol. Conversely, the oil that is the richest in free fatty acids is brought into contact with the alcohol that is the most charged with water.

Thus, the stress of the release of the water on the reaction equilibrium does not occur, which makes it possible to produce very high fatty acid conversion levels in a single reactive contactor by avoiding intermediate drying of the oil for removing the water that unfavorably influences the equilibrium of the reaction.

Said alcohol feedstock advantageously consists of the alcohol-rich phase drawn off from the contactor and recycled to said contactor, mixed with a supply of alcohol. Said alcohol phase that is drawn off from the contactor is advantageously treated before being recycled in such a way as to keep the water content at the desired value in said alcohol feedstock.

The alcohol-rich phase is also gradually enriched with free fatty acids. With this phase being advantageously recycled in the contactor, after optional distillation, the free fatty acids are also recycled and are therefore not lost.

Said contactor also comprises a system making it possible to maintain the dispersion of the light phase, for example and in a non-limiting manner, in the form of plates or packings, structured or unstructured.

In accordance with the invention, said liquid/liquid contactor is operated at a temperature of between 25 and 120° C., preferably between 25 and 100° C. With said process being performed in the liquid phase, the pressure is of only minor importance. Said liquid-liquid contactor is operated at a pressure that is adequate for keeping the phases in the liquid state, in a preferred manner between 1 and 20 bar absolute.

The ratio by mass of alcohol in said alcohol feedstock to oil feedstock is advantageously between 15/85 and 85/15, preferably between 20/80 and 80/20, and in a preferred manner between 40/60 and 60/40.

The contact time of the light phase and the heavy phase within said liquid/liquid contactor is at least 30 minutes and preferably less than 1 hour and 30 minutes.

The conversion of the free fatty acids contained in said oil feedstock into esters by the pretreatment process according to the invention is greater than 98%.

EXAMPLES

Example 1

According to the Prior Art

An oil feedstock containing a mixture of corn vegetable oil containing 10% by weight of free fatty acid is used for supplying an esterification system of fatty acids. The alcohol feedstock consists of dry methanol (water content<500 ppm).

1,000 kg/h of oil feedstock is supplied, as well as 225 kg/h of alcohol feedstock, in such a way as to obtain a molar ratio of 20/1 of methanol/oil at the entrance to the reaction section.

The catalyst is an Amberlyst BD20 sulfonic resin marketed by the Rohm & Haas Company. The acidic capacity of this solid is 1.2 mm of $H^+$ eq/g. The first reactor contains 1 $m^3$ of resin (hourly volumetric flow rate, or Liquid Hourly Space Velocity according to the English designation, LHSV=1.2 $h^{-1}$). The reaction takes place at 80° C. under a pressure of 20 bar. A conversion of 85% of the fatty acids is observed, which is inadequate for making the thus treated oil compatible with its use in an oil treatment process such as a process for hydrogenation of oils, or transesterification.

With the reaction having reached at the reactor outlet an advanced stage close to the thermodynamic equilibrium, it is necessary to remove one of the products of the reaction to achieve higher conversion of the fatty acids. Vacuum evaporation (230 mbar) is carried out so as to volatilize the unreacted methanol as well as the water that is formed by the reaction. It is noted that the vacuum that is achieved is obtained by a liquid ring pump operating with a vacuum pressure of 13 mbar. A second reaction stage is used, identical to the first stage, after adding 200 kg/h of methanol for completing the reaction. The measured conversion of the fatty acids at the end of the second reaction stage is 99%.

A final drying is implemented in the case where the water is incompatible for the downstream phases of upgrading of the product (for example, for its storage, with the water providing reactions for degradation of the oil that is not reacted in fatty acid).

Example 2

Counter-Current Esterification with Dry Methanol (According to the Invention)

An oil feedstock that is identical to the one of Example 1 is introduced into a vertical liquid/liquid counter-current contactor containing a catalyst of the TA 801 sulfonic resin type marketed by the Axens Company, of which the acidic capacity is 4.1 mmol of $H^+$ eq/g. The oil feedstock is introduced at the top of the contactor and constitutes the heavy phase.

The density of said oil feedstock is 0.917.

At the bottom of the contactor, the methanol feedstock, comprising methanol and 1% by weight of water, is introduced. A flow rate of 1,000 kg/h of alcohol feedstock is used, so as to be in the liquid/liquid equilibrium lens for the methanol/water/ester mixture. The alcohol feedstock constitutes the light phase.

The resin is arranged in two stages 2 m high, in a polymer-woven bag-type device making it possible to have an empty fraction per section of the contactor of approximately 60%. The two zones are separated by conventional separation internals (perforated grids).

The contactor is operated at a temperature of 50° C. and a pressure of 10 bar. The two counter-current separating stages implement overall 99.7% conversion of the fatty acids. The water that is produced is recovered in the upper phase of the contactor in the alcohol-rich light phase. Fatty acids are also present in said light phase. They are recycled in the contactor with the alcohol feedstock. A portion of the alcohol feedstock is distilled so as to keep the water content in said feedstock at 1% by weight.

The pretreated oil is recovered in the heavy phase that is drawn off at the bottom of the contactor. This oil does not contain water, but it contains approximately 5% by weight of methanol, which does not adversely affect the processes downstream from the treatment of oil (hydrotreatment or transesterification).

Example 3

Counter-Current Esterification with Wet Ethanol

An oil feedstock that is identical to that of Example 1 is introduced into a contactor that is identical to that of Example 2 containing the same catalyst as in Example 2. The oil feedstock is introduced at the bottom of the contactor and constitutes the light phase.

The alcohol feedstock, comprising 40% by weight of ethanol and 60% by weight of water, is introduced at the top of the contactor. The density of the alcohol feedstock is 0.935.

In a first experiment, the contactor is operated at a temperature of 60° C., at a pressure of 10 bar absolute, with a ratio by mass of the oil/ethanol feeds of 1. The conversion of the free fatty acids is 99%.

In a second experiment, the contactor is operated at a temperature of 50° C., at a pressure of 10 bar absolute, with a ratio by mass of the oil/ethanol feeds of 0.5. The conversion of the free fatty acids is 98.4%.

The oil-rich phase that is drawn off from said contactor, i.e., the pretreated oil, contains approximately 7% by weight of ethanol and 0.6% by weight of water.

The process according to the invention therefore makes it possible to carry out the esterification reaction in an almost-total way without intermediate drying, with wet ethanol, whereas water is an inhibitor of the reaction (product of a balanced reaction).

Example 4

Counter-Current Esterification with Dry Ethanol

An oil feedstock that is identical to that of Example 1 at the top of the contactor is introduced into a contactor that is identical to that of Example 2. An alcohol feedstock that consists of ethanol and 1% by weight of water is introduced at the bottom of the contactor.

In this case, the contactor is to be operated at low temperature with a low oil/ethanol ratio in such a way as to maintain the separation in the entire contactor.

The contactor is operated at a temperature of 50° C. with a ratio by mass of oil/ethanol of 1/5, at a pressure of 10 bar absolute. The conversion of the free fatty acids is 99.7%.

Because of the large excess of ethanol, the pretreated oil contains approximately 20% by weight of ethanol. However, the pretreated oil that is obtained is very dry, with a water content of 10 ppm.

The drawn-off alcohol-rich phase contains a small amount of ester and entrained acid (approximately 0.1% by weight relative to the alcohol). The water that is obtained from the reaction is also almost completely recovered in this flow.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding French Application No. 13/63080, filed Dec. 19, 2013 are incorporated by reference herein.

The invention claimed is:

1. Continuous process for pretreatment of an oil feedstock comprising at most 20% by weight of free fatty acids by esterification of free fatty acids in which a vertical liquid/liquid contactor containing an esterification catalyst in solid form is supplied in counter-current by an alcohol feedstock comprising at least 20% by weight of an alcohol and said oil feedstock, with said contactor being operated at a temperature of between 25 and 120° C., with said contactor performing the contact in liquid-liquid counter-current between a heavy phase and a light phase, with said heavy phase being able to be either an oil-rich phase or an alcohol-rich phase.

2. Process according to claim 1, in which said alcohol is methanol or ethanol.

3. Process according to claim 1, in which a water content of said alcohol feedstock is adjusted in such a way that said alcohol feedstock has a density that is greater than that of said oil feedstock.

4. Process according to claim 1, in which a water content of said alcohol feedstock is adjusted in such a way that said alcohol feedstock has a density that is lower than that of said oil feedstock.

5. Process according to claim 4, in which said contactor comprises at least one zone for collecting the light phase, a zone for collecting the heavy phase, a zone for bringing said heavy phase into contact with said catalyst, and a zone for redispersion of the light phase and the heavy phase.

6. Process according to claim 1, in which said esterification catalyst is selected from among silica-aluminas, acidic clays, a zirconia that may or may not be sulfated, and acidic resins, taken by themselves or in a mixture.

7. Process according to claim 6, in which said esterification catalyst is an acidic resin that has a cross-linking level of between 20 and 40%, and an acidic capacity of between 0.2 and 6 mmol of H⁺ equivalent per g.

8. Process according to claim 1, in which a ratio by mass of alcohol in said alcohol feedstock to oil feedstock is between 15/85 and 85/15.

9. Process according to claim 1, in which said alcohol feedstock consists of the alcohol-rich phase drawn off from the contactor and recycled to said contactor, mixed with an alcohol supply.

10. Process according to claim 9, in which said alcohol-rich phase drawn off from the contactor is treated before being recycled in such a way as to keep a water content at the desired value in said alcohol feedstock.

* * * * *